United States Patent [19]
Green et al.

[11] Patent Number: 6,096,219
[45] Date of Patent: Aug. 1, 2000

[54] METHOD AND APPARATUS FOR PRETREATMENT OF HAZARDOUS WASTE MATERIAL

[75] Inventors: Lawrence M. Green, Miami; Michael G. Nickelsen, Pembroke Pines, both of Fla.

[73] Assignee: Sanitrol Systems, Inc., Miami, Fla.

[21] Appl. No.: 09/076,609

[22] Filed: May 12, 1998

Related U.S. Application Data

[63] Continuation-in-part of application No. 08/745,511, Nov. 12, 1996, Pat. No. 5,811,014.

[51] Int. Cl.[7] ............................. C02F 1/78; A62D 3/00; B01J 19/12
[52] U.S. Cl. ..................... 210/695; 210/748; 210/750; 210/752; 210/760; 210/173; 210/192; 210/194; 210/199; 210/205; 422/24; 422/28; 422/186.01; 422/186.07; 422/186.3; 588/219; 588/227
[58] Field of Search ..................... 210/695, 748, 210/750, 752, 760, 764, 192, 194, 199, 205, 173; 422/22, 24, 28, 186, 186.3, 186.01, 186.07; 588/219, 227

[56] References Cited

U.S. PATENT DOCUMENTS

| | | | |
|---|---|---|---|
| 3,788,473 | 1/1974 | King | 210/112 |
| 4,946,590 | 8/1990 | Hertzog | 210/222 |
| 5,174,905 | 12/1992 | Shaw | 210/760 |
| 5,254,229 | 10/1993 | Ohmi et al. | 204/157.15 |
| 5,266,216 | 11/1993 | Agueda et al. | 210/258 |
| 5,308,480 | 5/1994 | Hinson et al. | 210/195.1 |
| 5,413,768 | 5/1995 | Stanley, Jr. | 422/186.3 |
| 5,417,852 | 5/1995 | Furness, Jr. et al. | 210/188 |
| 5,422,068 | 6/1995 | Shalaby et al. | 422/22 |
| 5,457,269 | 10/1995 | Schonberg | 588/212 |
| 5,466,367 | 11/1995 | Coate et al. | 210/96.1 |
| 5,603,972 | 2/1997 | McFarland | 426/240 |
| 5,679,257 | 10/1997 | Coate et al. | 210/695 |

*Primary Examiner*—David A. Simmons
*Assistant Examiner*—Betsey J. Morrison
*Attorney, Agent, or Firm*—Garrison & Associates PS; David L. Garrison

[57] ABSTRACT

The present invention provides a method for the pretreatment of hazardous biological and chemical contaminants from a waste fluid stream prior to discharge to a waste water treatment facility such as a publicly owned water treatment works or a similar privately operated facility. The method includes breaking apart tissue samples with a macerator, contacting a waste fluid stream with ozone, preferably in a vibrational mixer, which thereby acts as a promoter of hydroxyl radicals, passing the mixture through strong and weak unpolarized magnetic fields, static discharge and neutralization units, and finally, exposing the mixture to ultraviolet radiation. If found necessary, a subsequent static discharge and neutralization unit may be employed.

19 Claims, 3 Drawing Sheets

METHOD AND APPARATUS FOR PRETREATMENT OF HAZARDOUS WASTE MATERIAL

RELATED APPLICATIONS

This application is a continuation-in-part of our U.S. patent application Ser. No. 08/745,511 filed Nov. 12, 1996, now U.S. Pat. No. 5,811,014, issued Sep. 22, 1998.

FIELD AND BACKGROUND OF THE INVENTION

This invention relates to a process for the pre-treatment of contaminants from a flowing waste fluid, and more particularly to an apparatus and method utilizing a macerator, ozone ($O_3$), a vibrational mixer, a source of hydroxyl radicals (•OH), strong and weak unpolarized magnetic fields, static discharge units, and ultraviolet (UV) radiation to destroy contaminants.

There have long been various methods and devices for the treatment of biological and chemical contaminants in waste fluids. Large-scale water treatment facilities have been traditionally used for the treatment, removal, and processing of both human and low levels of industrial waste. With increased urbanization these same water treatment facilities have been required to additionally treat complex mixtures of toxic and hazardous material from both private and industrial users. As a result many of these same water treatment facilities are now unable to adequately treat the increased waste flow resulting in accidental or deliberate discharge of untreated material directly into the environment.

To combat the increased flow and more complex nature of current waste fluids, many wastewater utilities throughout the country require industrial generators of organic wastes high in biochemical oxygen demand (food waste, fats and oils, etc.,), recalcitrant xenobiotics (synthetic organic compounds foreign natural biological systems), heavy metals (Cd, Hg, Pb, etc.) and/or highly acid or alkaline pH to pre-treat their waste stream on-site prior to delivery to a waste water treatment facility. Although pre-treatment is required of many industries, liquid wastes generated by hospitals, medical facilities, medical examiners offices, healthcare offices, research facilities, nursing homes, food processing and animal handling facilities, diagnostic laboratories, veterinary clinics, analytical, chemical, microbiological, biotechnology and university laboratories in many instances are not required to pre-treat their collective wastewater stream even though this waste material is known to contain a variety of toxicogenic/mutagenic/teragenic/carcinogenic chemicals and viable, infectious, or genetically altered microbial pathogens. Many of the current pre-treatment units presently in use are expensive to operate, require trained personnel to maintain and require the use of caustic and/or toxic chemicals or expendable filters and cartridges which must be disposed of as a hazardous substance.

Examples of current methods include aeration stripping, ozone, chemical oxidation and reduction, high-energy beam (electron, gamma, and positron) irradiation, incineration, supercritical oxidation, carbon adsorption, filtration, and exposure to ultraviolet radiation. Some of these methods are currently employed, but many have not been generally accepted as standard practices due to their high equipment expense and cost of operation, size of equipment required, generation of toxic by-products and other similarly related problems.

An alternative treatment method is to use ozone in combination with exposure to ultraviolet radiation. Ozone has been used for more than sixty years for water treatment on the European continent. The role of ozone in waste fluid treatment may be classified as both an oxidant and a germicidal compound. There are at least four distinct recognized applications of ozone: (1) as a bactericide; (2) as a viricide; (3) as a powerful chemical oxidant; and (4) as a promoter of hydroxyl radicals when combined with ultraviolet radiation.

The potent germidal properties of ozone have been attributed to its high oxidation potential. Research indicates that disinfection by ozone is a direct result of bacterial cell wall disintegration. This is known as the "lysis phenomenon".

Ozone has several attributes in the treatment of waste fluids such as odor control, color removal, and iron and manganese removal. Ozone oxidizes inorganic substances completely and rapidly, e.g., sulfides to sulfates, and nitrites to nitrates. Of even greater importance is ozone's capability of breaking down complex organic chemicals. Oxidation of organic materials is more selective and incomplete at the concentrations and pH values of aqueous ozonation. Unsaturated and aromatic compounds are oxidized and split at the classical double bonds, producing carboxylic acids and ketones as products. Ozone also exerts a powerful and bleaching action on organic chemicals, which contribute to the color removal in waste fluids.

There are two principal mechanisms by which ozone may react with organic material. The first of these is a direct additive attack in which ozonides and ultimately peroxides are formed together with a splitting of the organic molecule. The other mechanism results from the decomposition of the ozone molecule, which is thought to proceed as follows:

  [1]

  [2]

  [3]

  [4]

  [5]

These three free radicals, ($HO_3$+•, __$HO_2$•, __•OH), especially •OH, are highly reactive and non-selectively oxidize all sorts of organic matter.

In the application of ozone combined with ultraviolet (UV) radiation, reaction [5] above becomes critically important. When the hydrogen peroxide ($H_2O_2$) formed in reaction [5] is exposed to ultraviolet light the following reaction takes place, which leads to the generation of additional hydroxyl radical (•OH).

  [6]

Many of these combined ozone/UV treatment systems are limited in their commercial application due to their relatively small scale and ability to deliver an adequate concentration of ozone and level of UV radiation sufficient for bacterial inactivation and chemical destruction. Typically these combined treatment systems have only been utilized for "in-home" domestic potable water treatment to remove taste and odor problems resulting from chlorination. As a result there has been considerable interest in improving ozone/UV treatment systems and techniques to allow for the treatment of more complex waste fluids at higher flow rates.

For example, U.S. Pat. No. 4,028,246 to Lund, et al, proposes a method by which a sewage effluent is simultaneously exposed to ozone and ultraviolet radiation followed by activated carbon adsorption filtration. The waste stream is then polished utilizing gamma irradiation.

Hellman, U.S. Pat. No. 4,687,574 describes a mobile water treatment device wherein the water is collected in a holding tank and subsequently passed through a screen to remove gross solids. The waste stream is then chemically treated in a flocculator to precipitate additional dissolved solids from the waste stream. The resulting mixture is then fed into a separator comprised of small plates or laminates to remove the precipitated solids. The remaining liquid waste is then sparged with ozone.

In U.S. Pat. No. 4,793,931, Stevens, et al, reveals a process for the treatment of waste containing solid or liquid phase contaminants The process includes chemical extraction of the waste contaminants using a perfluorinated solvent, separation of the perfluorinated solvent, and treatment of the remaining waste with a combination of ozone and exposure to UV radiation.

Johnson, et al, U.S. Pat. No. 4,563,286 describes a water purification system that employs the use of ionized allotropic forms of oxygen gas, ozone, and UV radiation. In this system the water being treated is simultaneously exposed to all three treatment techniques.

In its simplest form, Aqueda, et al, U.S. Pat. No. 5,266,216 shows a domestic water treatment apparatus in which only ozone is bubbled through the water column. Whereas, in U.S. Pat. No. 4,273,660, Beitzel exposes wastewater to ozone and UV radiation, while the wastewater is held in a cylindrical chamber containing a tubular UV lamp.

More complex treatment systems include a system designed by Feather, U.S. Pat. No. 4,414,924 for the removal of hydrogen sulfide and iron from well water. In this system, the treatment involves bubbling ozone and oxygen from a lower chamber through dilution control orifices to an upper chamber. In a counter current fashion the water flows into the lower chamber where the remaining traces of hydrogen sulfide are removed via additional ozone sparging. Inducing a vortex in the water column as it flows from the upper chamber to the lower chamber enhances effective contaminant oxidation. Further iron removal and water softening is achieved by passing the water stream through a magnetic field Thomas, Jr., U.S. Pat. No. 4,915,846 discloses a device, which precipitates dye particles from wastewater using an applied electric field. In U.S. Pat. No. 5,092,998, Satoh, also utilizes a strong electromagnetic field for the treatment of aqueous solution.

Furness, et al, in U.S. Pat. No. 5,417,852 describes a multi-step treatment system for removing contaminants from waste fluids. The method includes contacting a waste fluid stream with a promoter of hydroxyl radicals to entrain the promoter of hydroxyl radicals in the waste fluid stream, passing the waste fluid stream having the promoter of hydroxyl radicals entrained therewithin along a substantially tortuous path to allow the promoter of hydroxyl radicals to well within the waste fluid stream and to further entrain the promoter of hydroxyl radicals in the waste fluid stream, and irradiation the waste fluid stream with ultraviolet radiation.

Industrial wastewater treatment is described by Coate, et al, in U.S. Pat. No. 5,679,257. A wastewater treatment system is illustrated which can be configured to be portable and which minimizes the quantity of solids to be disposed of through the use of ozone for contaminant reduction to basic elements after the pH value of the wastewater to be treated is properly adjusted. This ozone, in one stage, is combined with ultrasound to cause coagulation and precipitation. In another stage ozone and ultraviolet light are used in a reduction process. Ion alignment using an electromagnetic field and an electrochemical flocculation process to which the wastewater is subjected causes further coagulation and precipitation. Throughout the "treatment train" filters are utilized to remove precipitated particulate matter.

OBJECTS OF THE INVENTION

It would be advantageous to provide an apparatus and process for the pretreatment of waste fluids containing hazardous and toxic materials such as viruses, bacteria, protozoa, human cells, and chemical contaminants without the use of cartridge filters, filter bags, feed chemicals, or other disposable or chemically hazardous expendable materials. This pre-treatment would be completed in such a way that renders the waste stream safe enough, and in compliance with existing federal, state, and local regulatory requirements, to be discharged into a conventional waste water treatment facility. It is also desirable that such a process and apparatus be highly reliable and efficient in operation while also being user friendly and extremely economical. Accordingly, the objectives of this invention include:

to make optimum use of the known reaction between ozone and dissolved and undissolved solids, chemicals, and bacterial wastes in water, in a multi-phase system and by means of a continuous process of ozone exposure, magnetic field treatment, mixing, ultraviolet treatment and interaction, between fluid to be treated and an oxidizing mixture, and static discharge and neutralization to render undesired impurities to provide an environmentally acceptable end product;

to provide a process for pre-treatment of hazardous biochemical and chemical mixtures which can accommodate substantial quantities of treatable solution in a relatively small and compact space, and within a relatively short period of time;

to provide a multi-stage, multi-phase system wherein solid matter is treated to suspend it in an aqueous suspension for facile treatment in an initial stage, and chemical and bacterial contaminants are treated in multiple diverse treatment stages, and further providing means for recirculating portions of the treated material through the system until the desired level of purification is reached to permit discharge into a waste water treatment facility; and, to provide a treatment system which can handle aqueous solutions of contaminated material, a slurry thereof or a combination of both forms of contaminated materials.

SUMMARY OF THE INVENTION

The present invention provides a method and apparatus to decompose aqueous-based organic compounds, precipitate selected heavy metals, and results in the destruction and/or deactivation of enteric viruses, enteric bacteria, and protozoans without the addition of chemicals or use of filters. The process also has direct applicability in the disinfection and treatment of aqueous medical waste (i.e., biologically active tissue media, diseased organs, blood and other bodily fluids) prior to discharge to a waste water treatment facility. Process benefits include: (1) applicability to a broad range of contaminants with concentration levels ranging from a few parts per billion (ppb) to saturation; (2) treatment independent of solution pH; (3) rapid elimination of organics (i.e., less than 20 seconds); (4) rapid destruction and/or deactivation of enteric viruses, enteric bacteria, and protozoans; (5) no air emissions; (6) no post-treatment of process effluent; (7) minimal electrical requirements (i.e., standard 120 V); and (8) scalability.

The process includes breaking apart tissue samples with a macerator, contacting a waste fluid with a strong oxidizing agent (i.e., ozone) in a holding/reaction vessel and causing the waste fluid to follow a multi-directional path providing an extended contact time for such an oxidant. At this stage in the process the oxidant begins degrading inorganic and organic contaminants and also results in the inactivation and/or cellular destruction of pathogenic microorganisms. The waste stream then passes through both in-line strong (10,000 Gauss) and weak (2,000 Gauss) un-polarized linear magnetic fields. Extensive analysis of existing technical literature on conventional magnetic treatment of water has demonstrated its effectiveness in several areas although very little is known of its mechanism of action. Magnetic fields created by natural or man-made permanent magnets, preferably forming the magnetic field of strength in the range of 2,000 to 10,000 Gauss results in a softening of the water. The invention contemplates use of a linear magnetic field having a nonpolar linear magnetic moment. In this application, it is theorized that the unpolarized linear magnetic fields alter the properties of the water by increasing its solvent capabilities. That is, aqueous streams exposed to the linear magnetic fields used in this invention have the ability to hold organic contaminants and dissolved materials in suspension at concentrations greater than nominal for a given temperature. The unpolarized magnetic fields also allow accelerated ozone diffusion, or greater mass transfer of the ozone, into the waste stream. With these two properties, enhanced contaminant suspension and greater mass transfer of the ozone, the strong and weak unpolarized magnetic fields greatly enhance the effectiveness of the contaminant treatment. It is also believed that the use of the magnetic fields will also increase the bactericidal function of the ozone. These fields also align the dipole moments of individual chemical compounds, including those compounds that make up the cellular membrane of microorganisms. This alignment is believed to allow transport of the ozone through the cellular membrane where it can effectively destroy the microorganism.

After passing through the unpolarized magnetic fields the waste fluid passes through an in-line device to remove any negative static charge imparted to the waste fluid such as by friction as the waste fluid passes through the system. The removal of this static buildup prevents or substantially reduces precipitation of inorganic constituents onto system components, reduces the corrosive nature of any undissolved ozone, and reduces the chances a static discharge which could ignite any highly volatile organic compounds that might be present in the waste fluid.

The waste fluid is then exposed to ultraviolet radiation. The UV radiation is utilized for several objectives: (1) further bacterial and viral inactivation; (2) further oxidation of organic chemical contaminants; (3) excitation of organic chemical contaminants making them more susceptible to oxidation, and; (4) the generation of hydroxyl radicals from unreacted ozone and hydrogen peroxide formed from the auto-decomposition of ozone. The ultraviolet radiation is applied to the waste material in a UV radiation chamber providing the necessary exposure and retention time needed to accomplish the objectives stated.

The waste fluid is then forced through a Mazzei injector. The vacuum end of the Mazzei injector is connected to the top of the holding/reaction vessel and is used to recover any of the unreacted ozone that had collected in the air space above the waste fluid in the holding/reaction vessel. This ozone is pulled into the flowing waste stream through the Mazzei injector and thus into intimate contact with the waste material. The mixture then passes through an in-line vibrational mixer. This mixer vibrates several hundred times per second as a result of the flowing waste stream. As a result of the intense vibration on the flowing waste stream, any large ozone bubbles are broken into much smaller bubbles. This process dramatically increases the surface area of the ozone bubbles and results in greater mass transfer of the ozone into the waste fluid.

The waste fluid then passes through a second UV radiation chamber or unit to complete the oxidation process, and then into a second in-line static discharge removal device before discharge of the waste material into a waste water treatment facility. The apparatus is also configured to recirculate part of all of the waste material in the event that additional treatment is required.

DETAILED DESCRIPTION OF THE INVENTION

Figure 1:
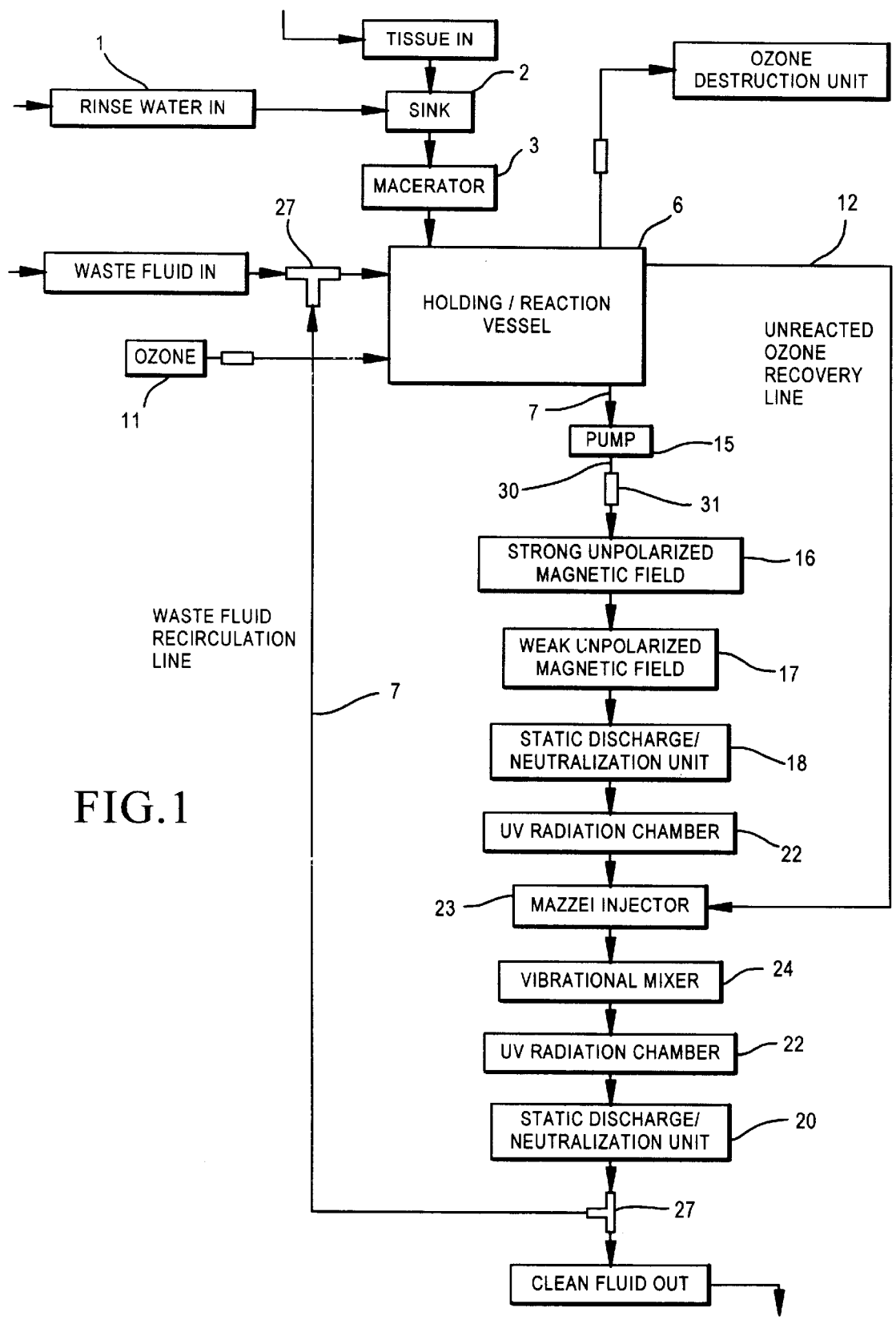
FIG. 1 is a schematic and block diagram of one embodiment of the present invention.

Throughout the following process and apparatus description similar parts have been indicated in the specification and drawings with the same reference numerals where appropriate. The drawings are not to scale and some sections have been enlarged for clarification purposes. All of the various control and monitoring electrical lines have been left out for clarity.

Since the apparatus and process being described has the capability of pre-treating liquid wastes and wastes containing solids (i.e., tissue, diseased organs, cellular material), the initial stages of pre-treatment are slightly different and will be described separately. After the initial stages of pre-treatment the balance of the process is the same for either type of waste stream. FIG. 1 is a schematic and block diagram describing the major components of the overall process. Specific details are shown in subsequent figures.

Figure 2:
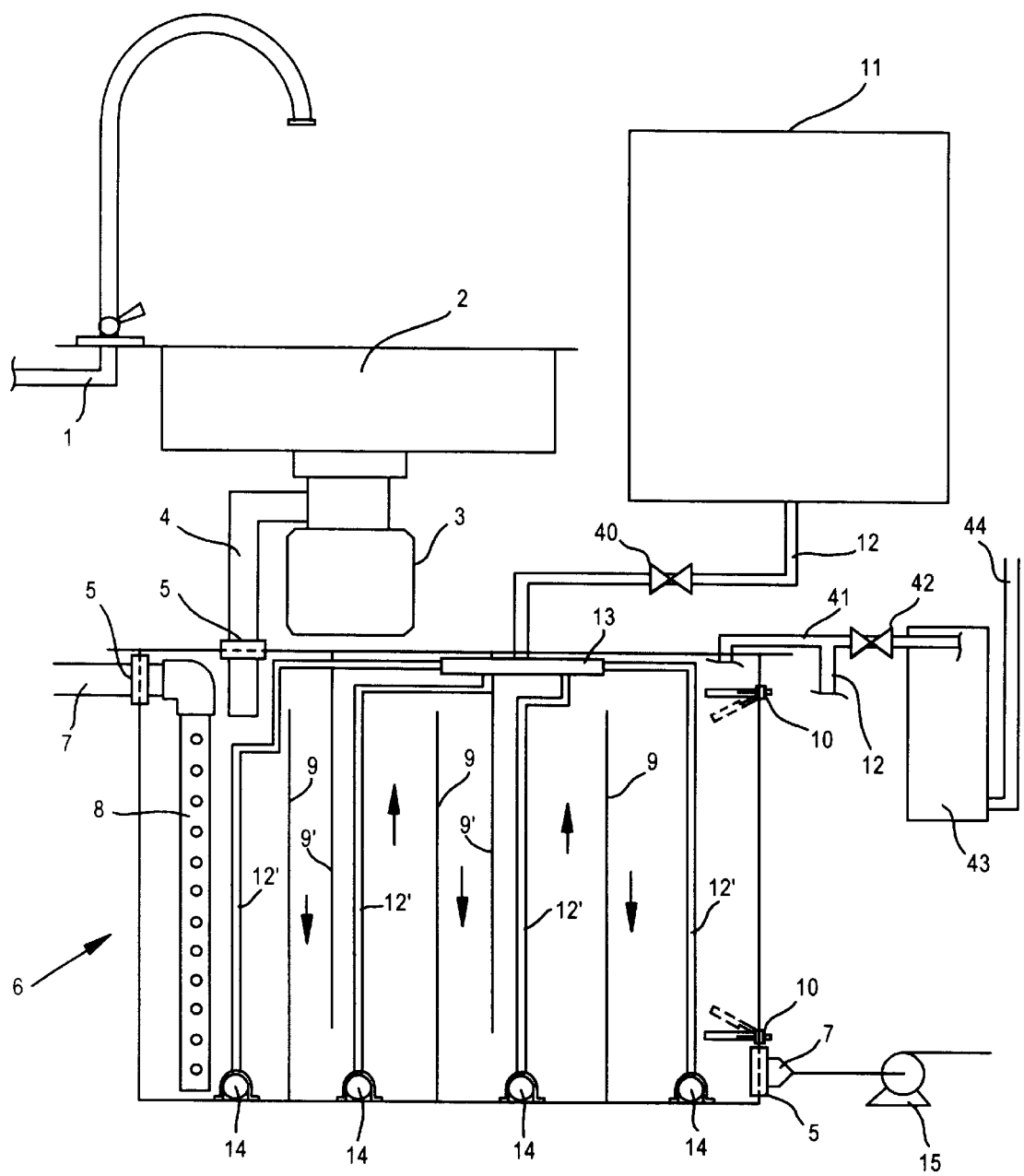
FIG. 2 is a detailed schematic depiction of the apparatus used in the initial steps of the pre-treatment process showing waste input, mixing, and ozone delivery in accordance with an embodiment of the present invention.

In FIG. 2, contaminated solid material (i.e., tissue, diseased organs, cellular material, etc.) is placed into a stainless steel sink 2 and is rinsed into the sink drain with tap water 1 and into a macerator 3 where the solid material is broken down and homogenized. The resulting waste mixture is discharged through a pipe 4 and passes into the holding/ reaction vessel 6 through a tank adapter 5. The sink, tank, and pipe and others in the system are preferably stainless steel or other chemically resistant plastics.

Whenever the contaminated materials do not need to be broken down and homogenized as in the preceding paragraph, the materials may be directly injected into the tank 6. Thus, aqueous contaminated waste fluid is received through a pipe or other conduit 7 and passes through a tank adapter 5 into the holding/reaction vessel 6 through a pipe 8, which extends toward the bottom of the holding/reaction vessel 6. The pipe 8 is perforated, preferably with multiple holes, which prevents siphoning of the waste fluid back through the pipe 8 when the system is operational. The perforations in this pipe 8 also may result in a venturi effect as the waste fluid passes through the pipe 8, drawing waste fluid that has already received some treatment in the holding/reaction vessel 6 back into the pipe 8, thereby enhancing solution mixing, contact time, and treatment efficiency.

The waste stream from either source is forced to flow through a multi-directional path within the holding/reaction vessel 6 due to baffles 9 and 9'. These baffles 9 and 9' greatly enhance the effectiveness of the ozone by increasing contact time. Forcing the waste fluid to follow his circuitous path also eliminates plug flow. Plug flow may occur whenever a portion of the waste fluid passes through the treatment process/step without being treated. When the level of waste material reaches a sufficient level to open a contact closure on a side-mount level switch 10, a relay is activated that starts an ozone generator 11 and ultraviolet radiation units 19.

An ozone generator 11 delivers a gaseous stream of ozone into the holding/reaction vessel 6 through an ozone delivery tube 12 through a check valve 40 to a distribution manifold 13. The distribution manifold 13 preferably delivers the ozone at a pressure of about 20 psi and a flow rate of about 50 SCFM through delivery tubes 12' to a plurality of sparging structures 14 mounted to the bottom of the holding/reaction vessel 6. The sparging structures 14 are composed of porous material (silica or chemically resistant cross-linked plastics), well known for bubbling gaseous material into liquids. Exhaust gas from the reaction vessel is vented through vent tube 41 and either passes to a subsequent stage of the process as described below or passes through a check valve 42 into an ozone destruction unit 43. The ozone destruction unit is preferable comprised of an 18" long by 2" diameter pipe filled with either a metallic oxide decomposer (i.e. $MnO_2$) and/or granular activated carbon. In either instance the ozone is catalytically destroyed forming oxygen which is then vented directly to the atmosphere at vent 44.

The waste fluid level continues to rise in the holding/reaction vessel or tank 6 until it reaches a sufficient level to close a contact closure on a second side-mount level switch 10. Upon closure of this contact, a relay is activated which starts a pump 15. The waste fluid is drawn from the bottom of the holding/reaction vessel 6 through a tank adapter 5 and pipe or similar conduit 7 into the pump 15. The pump 15 pushes the waste fluid through a pipe or similar conduit 30 and check valve 31 to the first of two magnetic treatment elements which are placed in cylindrical housings called N-Cells (see FIG. 3). Typically, the magnetic elements are cylindrical and housed within a stainless steel tubular housing. The stainless steel housing is then placed inside an inline flow device 19 such as that manufactured by V-U FLOW FILTERS, INC., shown schematically in FIG. 3. The first N-Cell 16 is a cylindrical structure containing magnetic material that subjects the waste fluid to a strong (10,000 Gauss) un-polarized linear magnetic field. This magnetic field is preferentially generated using ceramic, rare earth neodynium, or ALNICO (combined aluminum, nickel, and cobalt) magnets. The waste fluid then travels through a pipe or similar conduit 7 to the second N-Cell 17, which subjects the waste fluid to a weak (2,000 Gauss) un-polarized magnetic field.

Figure 3:
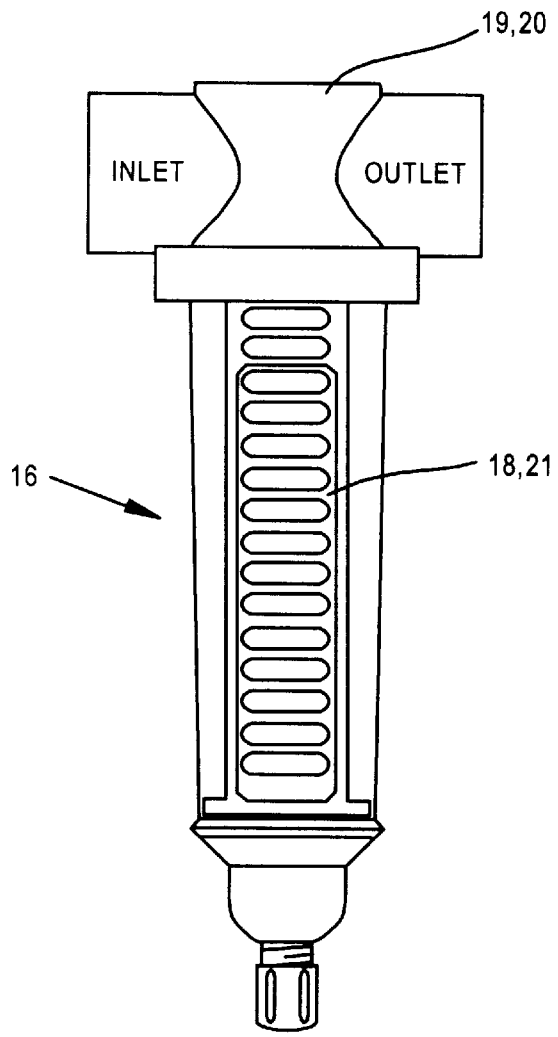
FIG. 3 is a schematic representation of the VU-Flow canisters utilized to house the N-Cells for the magnetic treatment steps and the solid zinc rods used in the static neutralization steps in accordance with an embodiment of the present invention.
Figure 4:
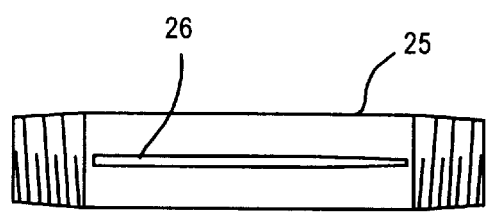
FIG. 4 is schematic describing the top and side cross-sectional views of the vibrational mixer in accordance with an embodiment of the present invention.
Figure 4A:
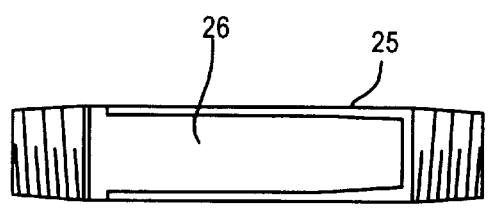

The waste fluid then travels through a pipe or similar conduit 7 to a third V-U Flow canister 20, which contains a solid cylindrical bar of zinc 21 (see FIG. 3). The zinc is used as a sacrificial anode and eliminates any static charge that may have accumulated in the flowing waste stream. The waste fluid then travels through a pipe or similar conduit 7 to the first of two ultraviolet (UV) radiation treatment units 22. The waste fluid then travels through a pipe or similar conduit 7 through a Mazzei injector 23 manufactured by MAZZEI INJECTION, CORP., a device well known in the prior art. The vacuum end of the Mazzei injector 23 is connected, by tubing 12, back to the top of the holding/reaction vessel 6. The purpose of this tubing is to recover any unreacted ozone that had bubbled through the waste fluid in the holding/reaction vessel 6. The recovered ozone is vacuumed into and mixes with the flowing waste stream and is pushed through a pipe or similar conduit 7 into a vibrational mixer 24. The vibrational mixer 24 is comprised of a stainless steel pipe 25 which has a thin stainless steel plate 26 mounted perpendicular to the flowing waste stream (see FIG. 4). The action of the flowing waste stream causes the stainless steel plate 26 to vibrate several hundred times per second. This oscillation breaks apart the large ozone bubbles that had been vacuumed into the Mazzei injector 23 into many tiny bubbles, thereby increasing the surface area of the ozone and very significantly enhancing mass transfer of the ozone into the waste stream.

The waste fluid then travels through a pipe or similar conduit to the second UV treatment unit 22. At this point in the pre-treatment process all of the ozone has been consumed by reaction with the contaminants in the waste fluid and/or decomposed forming hydroxyl radicals when exposed to the UV radiation.

The waste fluid then travels through a pipe or similar conduit to a fourth V-U Flow canister 18, which contains a solid cylindrical bar of zinc 21. As before, the zinc is used as a sacrificial anode and eliminates any static charge that may have accumulated in the flowing waste stream. The waste stream exits through a pipe or similar conduit, whereupon it is discharged as fully pre-treated waste.

Under some circumstances, depending on the nature of the contaminants involved, part of all of the waste stream may be redirected back into the holding/reaction vessel or tank 6 to be retreated through a tee 27 and pipe or similar conduit. This recirculation can be repeated several times or at varying ratios until the desired level of pretreatment has been achieved.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for the pre-treatment of liquid material comprising the steps of: exposure to ozone, exposure to strong and weak un-polarized magnetic fields, exposure to static discharge removal material, exposure to a promoter of hydroxyl radicals, and exposure to ultraviolet radiation.

2. The process of claim 1 wherein the step of exposure to static discharge removal material comprises the exposure of said liquid material to a sacrificial zinc anode.

3. The process of claim 1 wherein the step of exposure to strong and weak un-polarized magnetic fields comprises first exposing said liquid material to an un-polarized 10,000 Gauss magnetic field then exposing said liquid material to an un-polarized 2,000 Gauss magnetic field.

4. A multi-stage, multi-phase apparatus for removal of solid, chemical and bacterial waste from a contaminated aqueous solution, comprising, in combination:

a first stage, including means defining a reaction tank for initial ozone treatment of waste matter in a contaminated fluid;

an injection port for injecting an aqueous slurry of contaminated solids into said tank;

a nozzle means disposed in a lower portion of said tank for injecting ozone into said aqueous slurry in said tank;

ozone generator means for supplying ozone to said tank;

means to withdraw fluid from said tank into a fluid discharge line;

means for exposing said fluid withdrawn from said tank to a strong, unpolarized linear magnetic field in the range of 2000 to 10000 Gauss;

means to discharge and neutralize static in said waste material;

means to expose said waste material to ultraviolet light; and, means to inject further amounts of ozone into said waste material in a mixing apparatus, whereby contaminants in said waste material are neutralized or destroyed.

5. The apparatus of claim 4 further including means for recirculation of a predetermined quantity of mixed fluid to said tank, comprising a recirculation line connecting said outlet from said mixing apparatus to said tank for continuously recirculating part or all of said waste material to said tank.

6. The apparatus of claim 4, wherein static discharge and neutralization means is provided downstream of said mixer.

7. The apparatus of claim 4, wherein a weak unpolarized linear magnetic field treatment means is positioned downstream of said strong unpolarized magnetic field treatment means.

8. The apparatus of claim 4, wherein said tank contains serially spaced baffles in the path of flow of said waste material so as to cause intermixing of oxidant and waste material.

9. The apparatus of claim 4, wherein said means to inject further quantities of ozone comprises an ozone recovery line extending from said tank to a Mazzei injector positioned upstream from said mixer.

10. The apparatus of claim 4, wherein means is provided, downstream of said ultraviolet light means for degassing said mixed fluid.

11. The apparatus of claim 4 wherein said means to discharge and neutralize static in said waste material comprises a sacrificial zinc anode placed in direct contact with said contaminated aqueous solution.

12. In a multi-phase apparatus for removal of chemical and bacterial waste from a mixture of contaminated solids suspended in contaminated aqueous solution, the combination of:

a tank comprising a holding and reaction vessel;

means to place contaminated solids suspended in contaminated aqueous fluid into said tank;

a fluid discharge means from said tank;

a pump in said fluid discharge line for removing said fluid under pressure;

a first hollow cylindrical magnetic field means for exposing waste material received from said pump to a strong, unpolarized linear magnetic field in the range of 2000 to 10000 Gauss;

a second hollow cylindrical magnetic field means for exposing waste material received from said first magnetic field means for exposing waste material to a weak unpolarized linear magnetic field in the range of up to 2000 Gauss;

a static discharge and neutralization unit located downstream of said second magnetic field means to remove static from said waste material;

means for treating said waste material with ultraviolet light;

means to inject and mix unreacted ozone from said tank into said waste material downstream of said ultraviolet treatment means to complete purification thereof.

13. The apparatus of claim 12 further including a second ultraviolet treatment means and an additional static discharge and neutralization unit.

14. The apparatus of claim 12 further including a recycle means to recycle part or all of said waste material to said tank for reprocessing.

15. A method of pretreating contaminated aqueous materials having hazardous chemical and biological contaminants therein prior to discharge to a waste water treatment facility comprising the steps of:

breaking apart tissue and other solids in a macerator and combining said solids with water to form an aqueous waste material;

contacting said waste material with ozone in an ozone treatment tank;

passing said waste material through a strong unpolarized linear magnetic field;

passing said mixture through a static discharge and neutralization unit;

exposing said material to ultraviolet radiation in an ultraviolet radiation chamber;

injecting ozone into said material in a Mazzei injector;

subjecting said material and ozone to intense vibrational mixing in a vibrational mixer; whereby said contaminants in said material are rendered sufficiently innocuous for discharge of the material into a waste water treatment facility.

16. The method of claim 15 wherein said step of treatment in a magnetic field is conducted in a strong unpolarized magnetic field having a strength in the range of 2000 to 10000 Gauss.

17. The method of claim 15 further including the step of subjecting said material to a second linear unpolarized magnetic field having a strength of up to 2000 Gauss.

18. The method of claim 15 further including the steps of subjecting said material to a second ultraviolet radiation treatment and a second static discharge and neutralization step prior to discharge.

19. The method of claim 15 further including the step of recycling a portion of the treated material to the tank.

* * * * *